(12) United States Patent
Ayame (10) Patent No.: US 6,932,763 B2
(45) Date of Patent: Aug. 23, 2005

(54) ENDOSCOPE LIGHT SOURCE APPARATUS FOR SHIELDING CENTRAL REGION OF RAY BUNDLE EARLIER

(75) Inventor: Daisuke Ayame, Saitama (JP)

(73) Assignee: Fujinon Corporation, Saitama (JP)

( * ) Notice: Subject to any disclaimer, the term of this patent is extended or adjusted under 35 U.S.C. 154(b) by 179 days.

(21) Appl. No.: 10/396,464

(22) Filed: Mar. 26, 2003

(65) Prior Publication Data

US 2003/0220546 A1 Nov. 27, 2003

(30) Foreign Application Priority Data

Mar. 29, 2002 (JP) .......................................... 2002-094680

(51) Int. Cl.⁷ .................................................. A61B 1/06
(52) U.S. Cl. ....................................... 600/181; 600/180
(58) Field of Search ................................. 600/180–181; 362/552, 574, 277

(56) References Cited

U.S. PATENT DOCUMENTS

| | | | | |
|---|---|---|---|---|
| 4,706,657 A | * | 11/1987 | Miyagi | ........................ 600/178 |
| 5,621,498 A | * | 4/1997 | Inoue et al. | ................... 355/67 |
| 6,367,958 B1 | * | 4/2002 | Jones | ........................... 362/552 |
| 6,629,925 B2 | * | 10/2003 | Kurosawa et al. | ........... 600/180 |
| 2001/0029318 A1 | * | 10/2001 | Honda et al. | ................ 600/180 |

* cited by examiner

Primary Examiner—John Leubecker
Assistant Examiner—Philip R Smith
(74) Attorney, Agent, or Firm—Snider & Associates; Ronald R. Snider (57) ABSTRACT

An aperture mechanism of this apparatus is provided with an aperture blade which has, for example, an outline converging toward the front end with a shielding width of the front-end blade section smaller than the diameter of a ray bundle transmitted into a light guide to achieve desired dimming by shielding the light in proximity of the central region in the ray bundle earlier than that in the outer regions. Thus, a relatively narrow distribution of light will be radiated onto an observed object for a long-distance examination of smaller aperture quantities and a wide distribution of illumination light will be radiated for a short-distance examination of larger aperture quantities. In addition, the aperture mechanism may be configured to move a small-circle aperture blade which is smaller than the cross-sectional area of the ray bundle disposed on the optical axis in the direction of optical axis to shield the light in proximity of the central region in the ray bundle earlier than that in the outer regions.

6 Claims, 9 Drawing Sheets

FIG. 9(A) FULL-OPEN

FIG. 9(B) INTERMEDIATE

FIG. 9(C) FULLY-CLOSED

ENDOSCOPE LIGHT SOURCE APPARATUS FOR SHIELDING CENTRAL REGION OF RAY BUNDLE EARLIER

BACKGROUND OF THE INVENTION

This application claims the priority of Japanese Patent Application No. 2002-94680 filed on Mar. 29, 2002 which is incorporated herein by reference.

1. Field of the Invention

The present invention relates to an endoscope light source apparatus which supplies source light to the front end of an endoscope through a light guide for illuminating an observed object and achieves aperture control over the source light.

2. Description of the Prior Art

An endoscope apparatus uses an endoscope for optically examining an observed object through an eyepiece or an electronic endoscope for imaging an observed object with a solid state imaging device or charge coupled device (CCD) and examines the observed object irradiated with illumination light, which is supplied by a light source apparatus. More specifically, source light from the light source apparatus is guided to the front end of the electronic endoscope via a light guide and the illumination light is radiated from the front end so that the observed object can be examined.

BRIEF SUMMARY OF THE INVENTION

However, the prior endoscope light source apparatus described above has been configured to provide a uniform distribution of light radiated from the endoscope front end within an illumination field at a relatively short distance, but on the other hand, a nonuniform distribution of light may be produced within an illumination field at a relatively long distance.

Figure 10A:
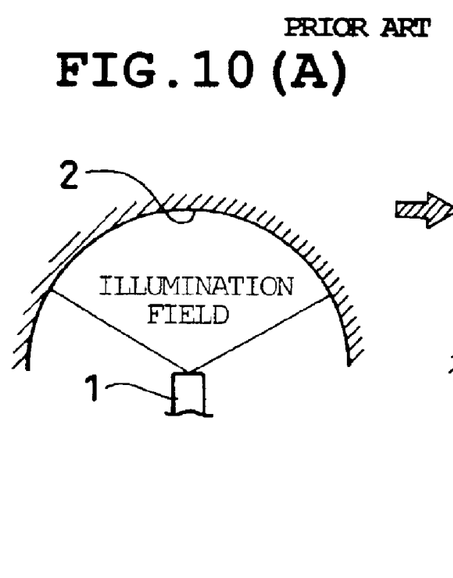
FIG. 10(A) shows long-distance illumination applied to an observed object by an endoscope.
Figure 10B:
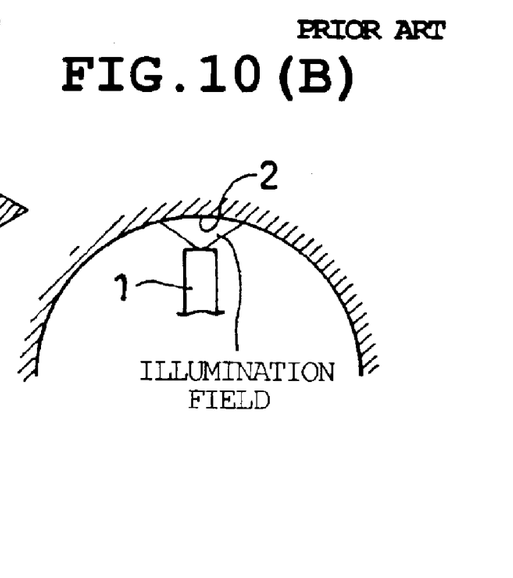
FIG. 10(B) shows short-distance illumination applied to the observed object by the endoscope.

FIG. 10(A) shows long-distance illumination for an endoscope examination and FIG. 10(B) shows short-distance illumination. An observed object 2 to be examined with an endoscope 1 may be often a digestive organ situated within a body cavity and have spherical or elliptical concaves or deep tubular inside surfaces and, for example, for long-distance illumination, the observed object 2 may have a concave illumination field as shown in FIG. 10(A).

Figure 11:
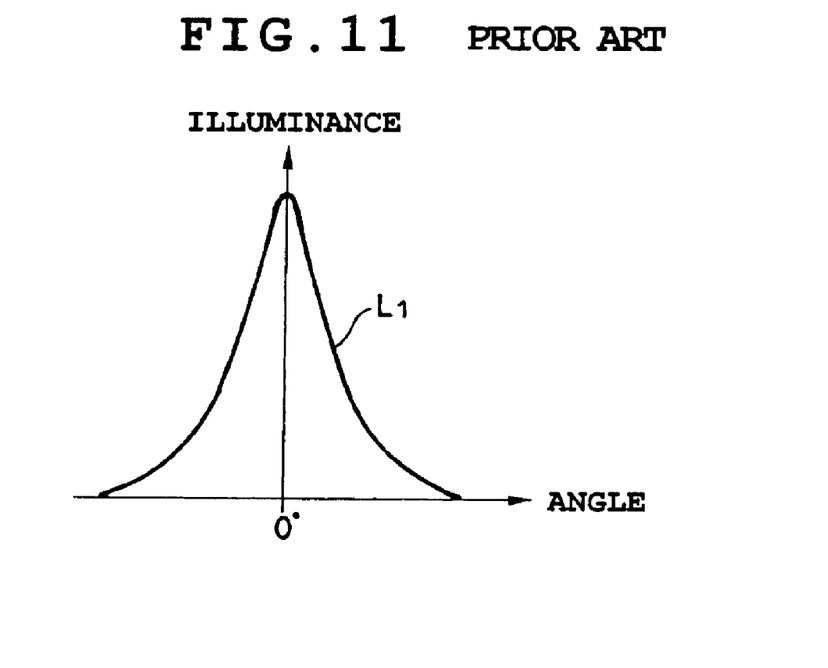
FIG. 11 shows characteristic curves of the distribution of incident angle for incoming light (in illuminance) transmitted into a light guide in a prior apparatus.

FIG. 11 shows a distribution of incident angle for incoming light transmitted into a light guide of a prior apparatus and as shown by a characteristic curve $L_1$ in the figure, the incoming light transmitted into the light guide exhibits the highest illuminance at an angle of 0° with respect to the optical axis (that is, on the optical axis of source light) and lower illuminance at larger angles (that is, rays of light radiated at larger angles with respect to the optical axis exhibit lower illuminance).

Figure 12:
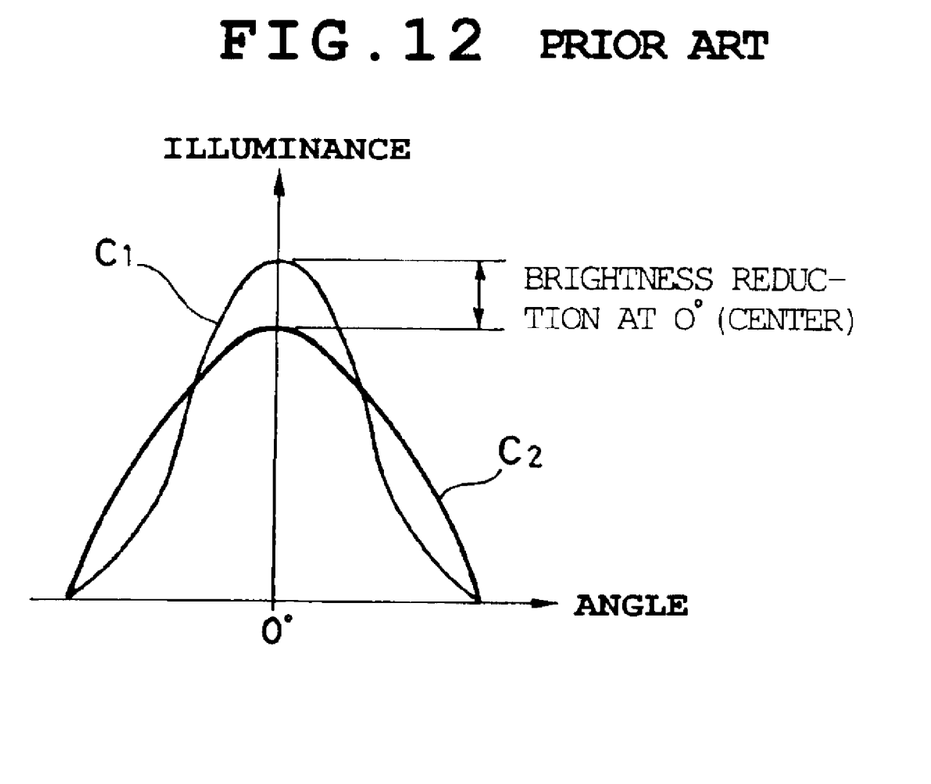
FIG. 12 shows characteristic curves of the distribution of light (emission angle distribution) for outgoing light (in illuminance) through an illumination lens provided on the endoscope front end in the prior apparatus.

FIG. 12 shows a distribution of light (emission angle distribution) for outgoing light through an illumination lens (aperture) provided on the endoscope front end of the prior apparatus and if the apparatus has been configured to be satisfactory to long-distance illumination, as shown by a characteristic curve $C_1$ in the figure, the outgoing light exhibits a narrow distribution in which the illuminance is higher at smaller angles in proximity of the optical axis (0°) and lower at larger angles. This means that such an intense light disposed in the central region can allow an observed object having concaves or deep tubular inside surfaces to be examined with satisfactorily bright illumination.

However, as shown in FIG. 10(B), when the endoscope 1 is close to the observed object 2, the observed object 2 within the irradiation field appears to be flat and then, illumination with an intense light disposed in the central region as shown by the characteristic curve $C_1$ in FIG. 12 may make a major difference in brightness between the central region and the surrounding regions in an image, resulting in inadequate brightness in the surrounding regions as compared with the central region. Therefore, for short-distance examinations including close examinations, it may be desirable that, contrarily to the characteristic curve $C_1$, the outgoing light exhibits a wide distribution in which the illuminance is lower in the central region and higher in the surrounding regions as shown by a characteristic curve $C_2$ in FIG. 12.

In view of the above disadvantages, it is an object of the present invention to provide an endoscope light source apparatus which radiates a narrow distribution of illumination light with much higher illuminance in proximity of the central region for long-distance examinations and a wide distribution of illumination light for short-distance examinations so that an observed object at any distance can be examined with satisfactorily bright illumination.

In order to attain the above and other objects, an endoscope light source apparatus according to an embodiment of the present invention comprises a condensing optical system for condensing source light, a light guide for guiding the light from the condensing optical system to the endoscope front end, an aperture blade disposed between the light guide and the above-described condensing optical system and having such a shape that an area of less than 180° in the outer regions of a ray bundle from the condensing optical system to the light guide is shielded when its blade section with a shielding width smaller than the diameter of the ray bundle is located at the center of the ray bundle (optical axis), and an aperture driving circuit for driving the above-described aperture blade so that light in proximity of the central region of the ray bundle is shielded earlier than that in the outer regions during dimming.

According to this embodiment of the present invention, the aperture blade has, for example, an outline (circumferential shape) converging toward its front end and the width of the front-end blade section is smaller than the diameter (width) of the ray bundle, and thus, when the aperture blade is driven, the front-end blade section of a smaller width moves toward the center of the ray bundle (optical axis). Then, the aperture blade converging toward its front end will shield the central region of the ray bundle earlier with the outer regions of the ray bundle left unshielded, so that the ratio of light within the central region of the ray bundle at smaller angles with respect to the optical axis may become smaller with that of light within the outer regions of the ray bundle at larger angles with respect to the optical axis becoming larger, as the dimming proceeds. Consequently, a relatively narrow distribution of light will be radiated onto an observed object for a long-distance examination of smaller aperture quantities and a wide distribution of illumination light will be radiated for a short-distance examination of larger aperture quantities, so that the whole observed object at short to long distances can be examined with satisfactorily bright illumination.

An endoscope light source apparatus according to another embodiment of the present invention comprises a condensing optical system, a light guide, an aperture blade disposed substantially on the optical axis between the light guide and the above-described condensing optical system and having an area smaller than the cross-sectional area of a ray bundle from the condensing optical system to the light guide, and an aperture moving mechanism for moving the above-described aperture blade so that light in proximity of the central region of the ray bundle is shielded earlier than that in the outer regions during dimming.

According to this embodiment of the present invention, the aperture blade having an area smaller than the cross-sectional area of the ray bundle is disposed on the optical axis in the form of a circular aperture blade, and then the circular aperture blade may be moved from the source lamp side toward the light guide side to dim the source light. This circular aperture blade may allow the ray bundle to be shielded from the central region to the outer regions in sequence, thereby resulting in a higher shielding ratio particularly in the central region.

Still another embodiment of the present invention comprises a condensing optical system, a light guide, and an aperture mechanism having an aperture blade disposed between the light guide and the above-described condensing optical system for operating the above-described aperture blade so that a full-open aperture can produce a narrow distribution of light with an intense light disposed in the central region and a dimming aperture can produce a wide distribution of light with the central light dimmed as the dimming proceeds.

DETAILED DESCRIPTION OF THE PREFERRED EMBODIMENTS

1. First Embodiment

Figure 1:
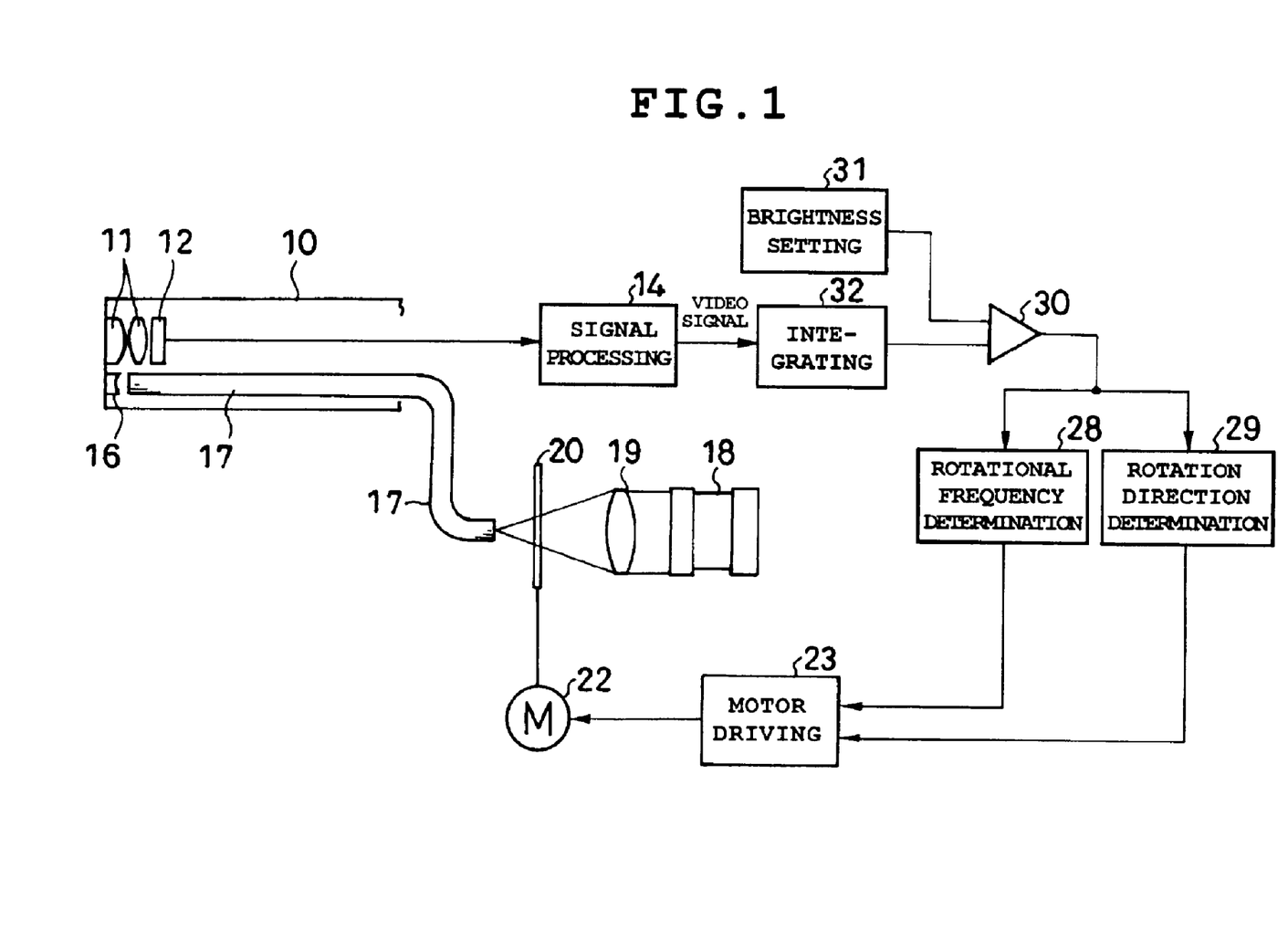
FIG. 1 is a block diagram for showing the configuration of an endoscope light source apparatus according to a first embodiment of the present invention.

FIG. 1 shows the configuration of an electronic endoscope apparatus which uses an endoscope light source apparatus according to a first embodiment of the present invention and FIG. 2 shows an aperture mechanism according to the first embodiment. In FIG. 1, a solid state imaging device or CCD 12 is provided on the front end of an electronic endoscope 10 via an objective lens 11 and a signal processing circuit 14 (provided for a processor device) for color image processing is connected to the CCD 12. A light guide 17 is also provided on the front end of the electronic endoscope 10 through an illumination lens 16 and runs to a light source apparatus (unit). Two illumination lenses 16 may be provided on the end face and in this case, the above-described light guide 17 will be divided on its way and guided to the two illumination lenses 16.

In the light source apparatus, a light source 18 such as a xenon lamp or halogen lamp, a condensing optical system 19, and an aperture blade 20 are provided, so that light from the light source 18 is transmitted into the light guide 17 via the aperture blade 20. In addition, a rotary motor 22 and a motor driving circuit 24 are also provided for rotating the above-described aperture blade 20.

Figure 2A:
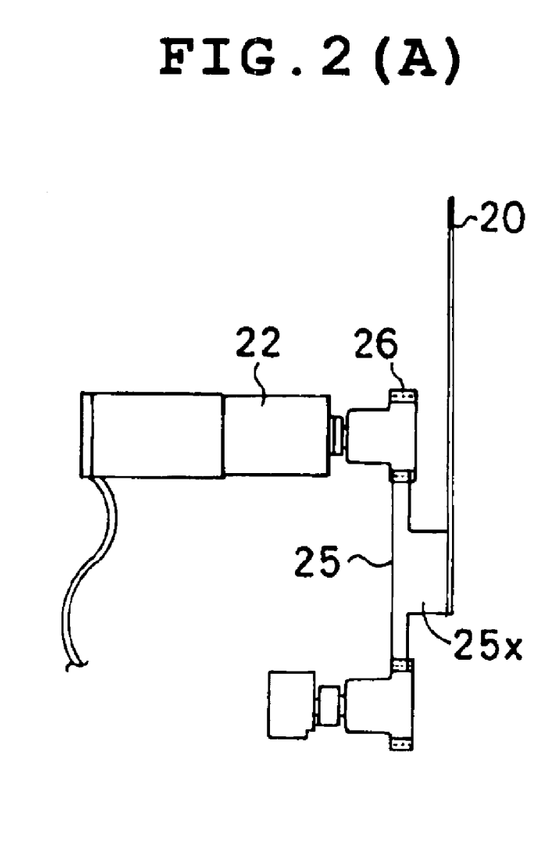
FIG. 2(A) is a side view for showing the configuration of an aperture mechanism according to the first embodiment.
Figure 2B:
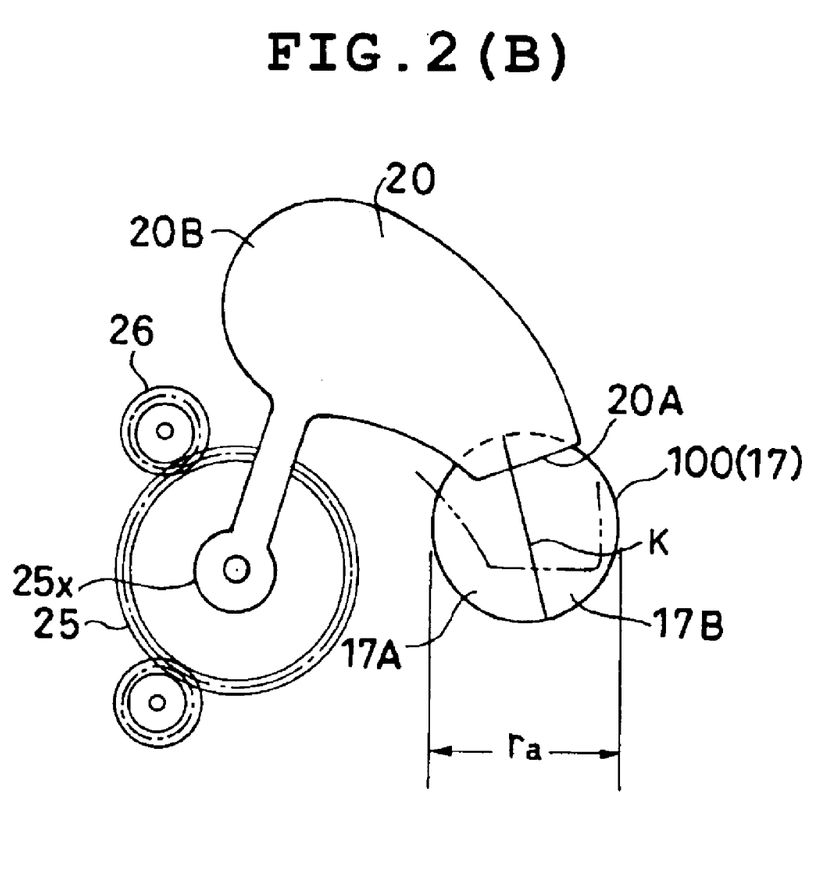
FIG. 2(B) is a front view of the aperture mechanism in FIG. 2(A)

In FIG. 2(B), the aperture blade 20 is shaped to have an outline converging toward the front end from a base section 20B which is enough large to fully shield a ray bundle 100 from the condensing optical system 19 and the front-end blade section 20A has a width smaller than the diameter $r_a$ of the ray bundle 100. The aperture blade 20 is mounted on a supporting gear 25 and is connected to a motor 22 via a motor gear 26 as shown in FIG. 2(A). The aperture blade 20 of such shape rotates about a gear shaft 25x to shield the ray bundle 100 from the central region with the outer regions left unshielded, as appreciated from a dashed line in the figure. The front-end blade section 20A of the aperture blade 20 may have a width smaller than that shown in the figure or may have an outline converging like two edges of a triangle.

When the light guide 17 is divided on its way for the two illumination lenses 16 on the endoscope end face as described above, two divided optical fiber bundles are provided at the incident end of the light guide 17. FIG. 2(B) shows these divided fiber bundles when the above-described ray bundle 100 is placed in front of the light guide 17 and they are viewed from the front, and as shown in the figure, the ray bundle 100 is divided into a first fiber bundle 17A and a second fiber bundle 17B. In this example, a dividing line K between the first fiber bundle 17A and the second fiber bundle 17B is positioned in conformity with the rotation direction of the aperture blade 20 (that is, positioned in the direction of a tangent to the rotation trajectory) so that both fiber bundles 17A and 17B can be shielded equally by the aperture blade 20.

In FIG. 1, a rotational frequency determination circuit 28 and a rotation direction determination circuit 29 are connected to the motor driving circuit 23 and a brightness setting circuit 31 and an integrating circuit 32 are connected to the determination circuits 28, 29 via a comparator circuit 30. More specifically, for example, the integrating circuit 32 receives a video signal from the above-described signal processing circuit 14 to provide an integrated signal for the luminance of an image and the above-described comparator circuit 30 compares an output signal from the integrating circuit 32 with a brightness reference signal established by the brightness setting circuit 31 to provide a brightness control signal. Then, based on the brightness control signal, the above-described rotational frequency determination circuit 28 determines a rotational frequency and the rotation direction determination circuit 29 determines a rotation direction and the resultant control signals are supplied to the motor driving circuit 23. Thus, the motor 22 is driven by the motor driving circuit 23 to drive the aperture blade 20 in the direction for dimming when the image brightness is too high and in the direction for intensifying when the image brightness is too low.

Figure 3:
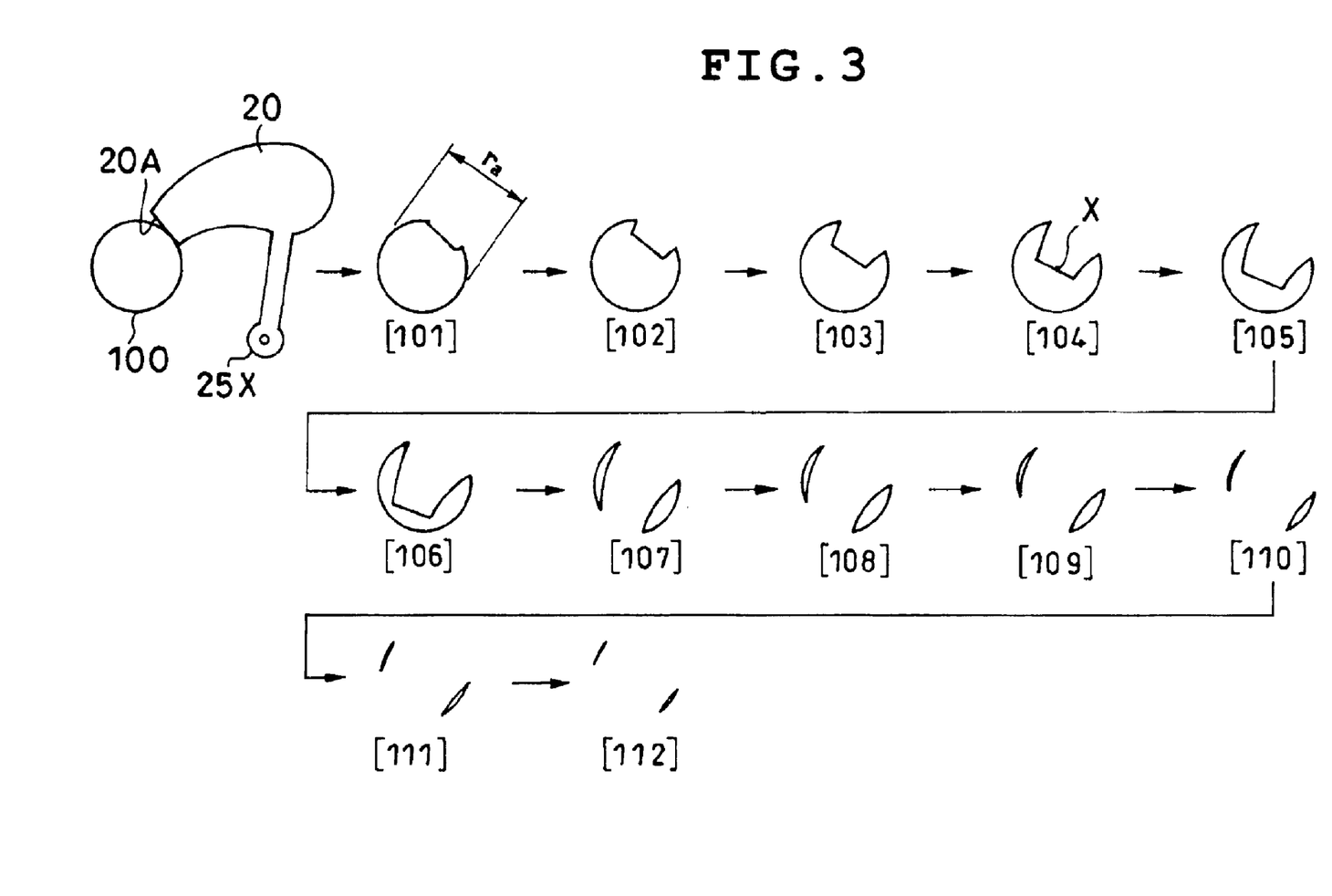
FIG. 3 shows the sequential steps of shielding a ray bundle through the aperture mechanism according to the first embodiment.

The first embodiment is configured as described above to cause the above-described aperture blade 20 to shield the ray bundle 100 according to the steps shown in FIG. 3. More specifically, the aperture blade begins to enter the ray bundle 100 at the front-end blade section 20A and as shown in steps 101 to 112, it shields the central region of the ray bundle 100 earlier with the outer regions left unshielded because the front-end blade section 20A has a width smaller than the diameter $r_a$ of the ray bundle 100. As appreciated from step 104 in FIG. 3, even when the front-end blade section 20A passes through the ray bundle center (optical axis) X, an area (outer area in cross section) of less than 180° in the outer regions of the ray bundle 100 is only shielded. Since the aperture blade 20 has an outline converging toward the front end and thus broadening toward the rear end, the outer regions of the ray bundle 100 are also shielded gradually to achieve desired shielding (dimming) of the ray bundle 100.

Figure 4:
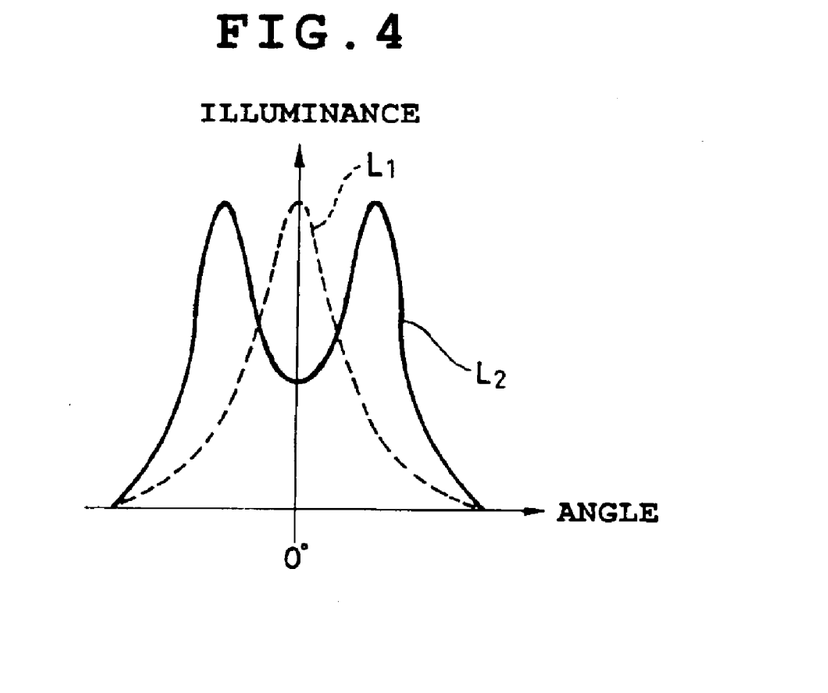
FIG. 4 shows characteristic curves of the distribution of incident angle for incoming light (in illuminance) transmitted into a light guide in the first embodiment.

FIG. 4 shows characteristic curves of the distribution of incident angle for incoming light transmitted into the light guide 17 during the above-described dimming through the aperture blade 20 and, for example, when the aperture blade 20 is moved as shown by step 104 or 105 in FIG. 3 during a short-distance examination, a distribution as shown by the characteristic curve $L_2$ in FIG. 4 is produced. More specifically, as compared with the characteristic curve $L_1$ which is satisfactory to long-distance examinations, the produced distribution shows that the illuminance is lower in proximity of the optical axis (X) at an angle of 0° and higher at intermediate angles.

Figure 5:
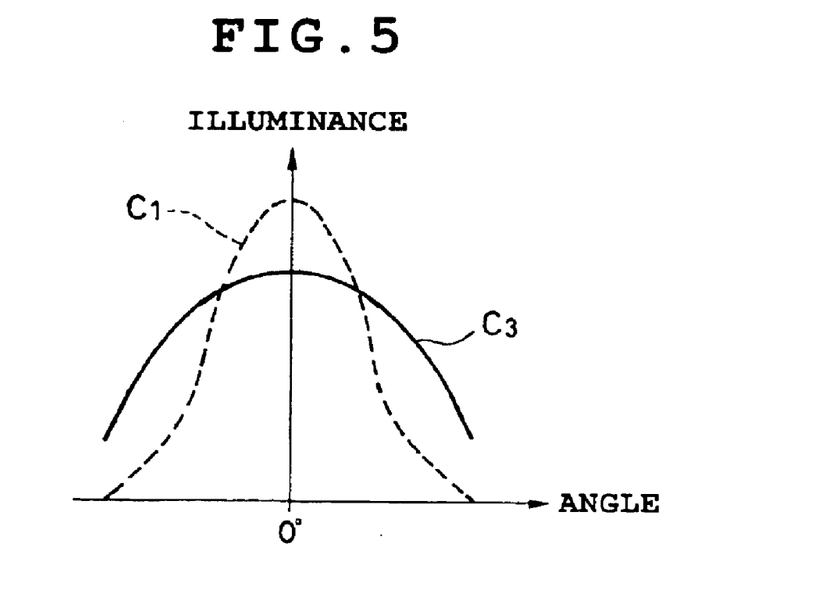
FIG. 5 shows characteristic curves of the distribution of light (emission angle distribution) for outgoing light (in illuminance) through an illumination lens provided on the endoscope front end in the first embodiment.

FIG. 5 shows characteristic curves of the distribution of light (emission angle distribution) for outgoing light through the illumination lens 16 (implemented by a flat concave lens) of the electronic endoscope 10 in this example, and the light as shown by the characteristic curve $L_2$ in FIG. 4 produces a distribution as shown by a characteristic curve $C_3$ in FIG. 5, which is a wide distribution of light similar to that of the characteristic curve $C_2$ in FIG. 12. More specifically, when the ray bundle is not shielded by the aperture blade 20, the light exhibits a distribution as shown by the characteristic curve $C_1$ which is satisfactory to long-distance examinations, and when the ray bundle is shielded by the aperture blade 20, the light exhibits a distribution as shown by the characteristic curve $C_3$ which is satisfactory to short-distance examinations, thereby providing satisfactory illumination light for not only long-distance examinations but short-distance examinations.

With the configuration in FIG. 1, for example, when a luminance signal in the video signal provided by the signal processing circuit 14 is integrated by the integrating circuit 32, the integrated signal and a brightness reference signal provided by the brightness setting circuit 31 are compared with each other by the comparator circuit 30 to provide a brightness control signal to the rotational frequency determination circuit 28 and the rotation direction determination circuit 29. Rotational frequency and rotation direction control signals provided by these circuits 28, 29 allow the motor driving circuit 23 to drive and rotate the motor 22 so that the aperture blade 20 is driven in the direction for dimming when the image is too bright and in the direction for intensifying when the image is dark, thereby resulting in satisfactorily bright images.

As described above, according to the first embodiment, since the aperture blade has, for example, an outline converging toward the front end and a shielding width of the front-end blade section is smaller than the diameter of source light bundle and the light in proximity of the central region in the ray bundle is shielded earlier than that in the outer regions during dimming, a relatively narrow distribution of illumination light with much higher illuminance in proximity of the central region for long-distance examinations as well as a wide distribution of illumination light for short-distance examinations can be radiated, so that the whole observed object at short to long distances can be examined with satisfactorily bright illumination.

Second Embodiment

Figure 6A:
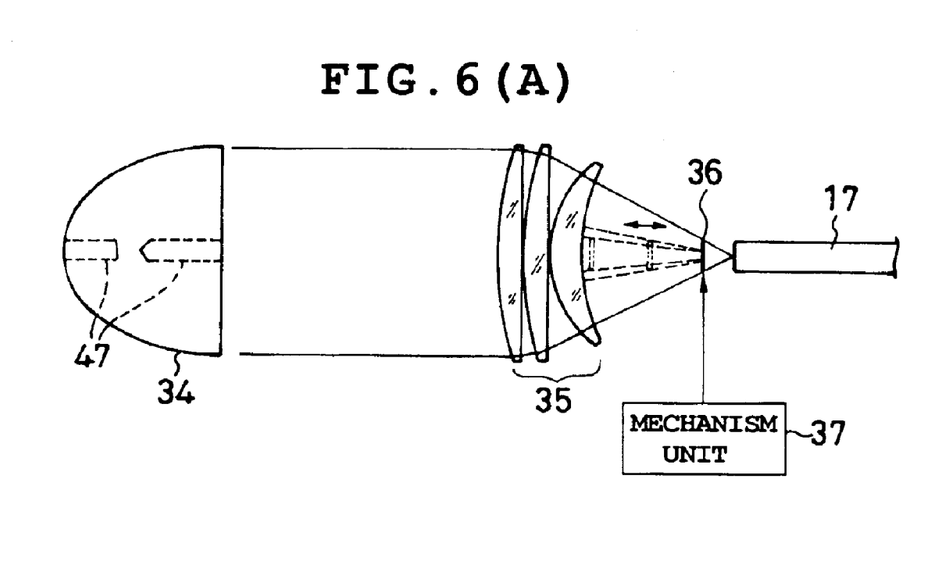
FIG. 6(A) is a side view for showing the configuration of an endoscope light source apparatus according to a second embodiment of the present invention.

FIG. 6 shows the configuration of an endoscope light source apparatus according to a second embodiment of the present invention and FIGS. 7 and 8 show aperture mechanisms according to the second embodiment. In FIG. 6(A), a condensing optical system 35 is provided in front of a light source (for example, a xenon lamp) 34 and a small-circle aperture blade (plate) 36 which has an area smaller than the cross-sectional area of a ray bundle 100 is provided between the condensing optical system 35 and a light guide 17 and driven by a mechanism unit 37.

Figure 7A:
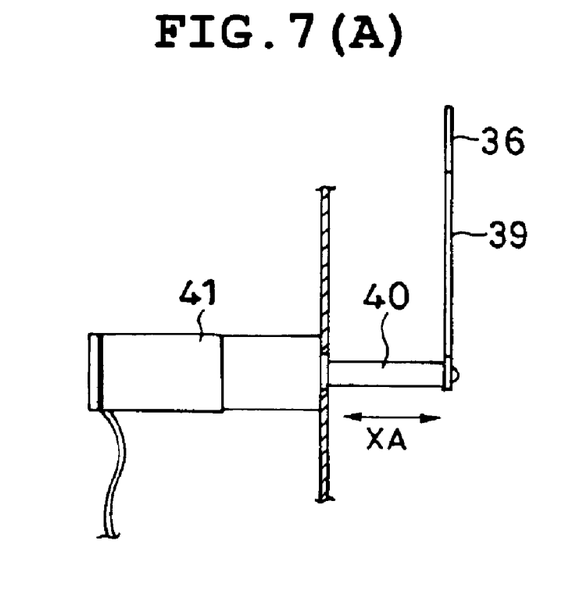
FIG. 7(A) is a side view for showing a configuration of an aperture mechanism according to the second embodiment.
Figure 7B:
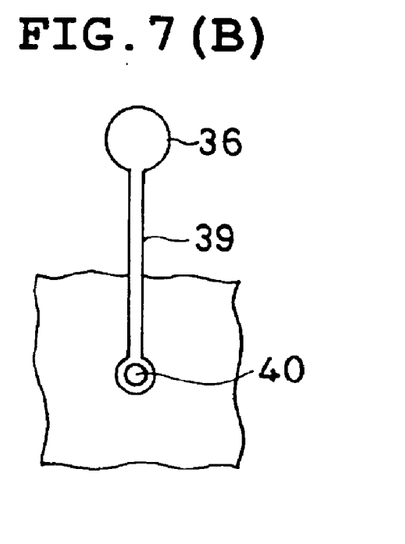
FIG. 7(B) is a front view of the aperture mechanism in FIG. 7(A)

FIGS. 7(A) and 7(B) show an example of the above-described aperture mechanism (37), which uses a linear induction motor. More specifically, the small-circle aperture blade 36 as shown is formed integral with a support member 39, which is mounted on a driving shaft 40 connected to a linear induction motor 41. With the aperture mechanism in FIGS. 7(A) and 7(B), when the motor 41 is driven, the driving shaft 40 is moved linearly in the horizontal direction, thereby moving the aperture blade 36 in the direction of optical axis XA.

Figure 8A:
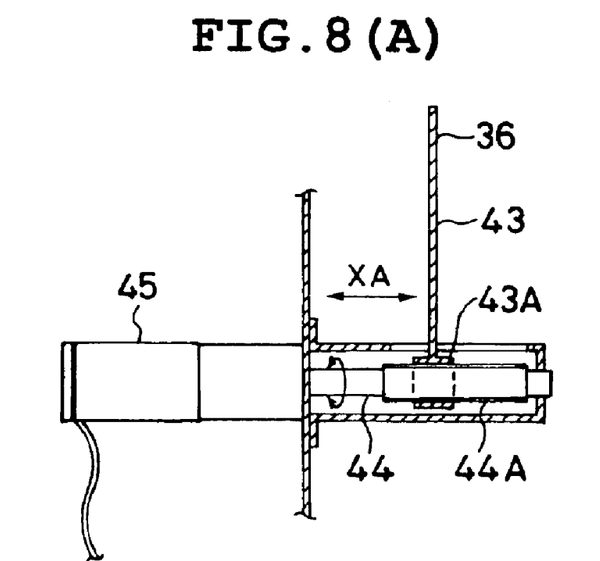
FIG. 8(A) is a side view for showing another configuration of the aperture mechanism according to the second embodiment.
Figure 8B:
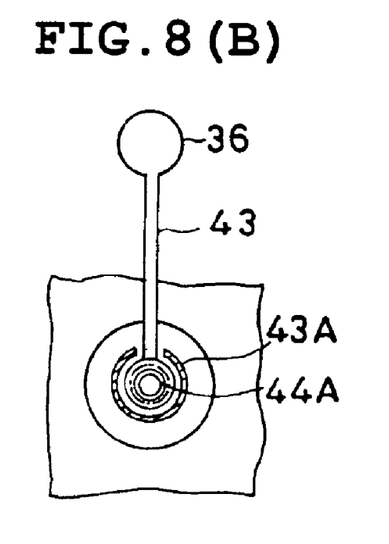
FIG. 8(B) is a front view (partly in section) of the aperture mechanism in FIG. 8(A)

FIGS. 8(A) and 8(B) show another example of the above-described aperture mechanism (37), which uses a rotary motor. More specifically, the small-circle aperture blade 36 is formed integral with a support member 43 which has a female-threaded cylinder 43A in the lower portion and a driving shaft 44 which has a male-threaded section 44A to be spirally coupled to the above-described female-threaded cylinder 43A is connected to a rotary motor 45. With the aperture mechanism in FIGS. 8(A) and 8(B), when the motor 45 rotates, driving shaft 44 rotates accordingly to move the aperture blade 36 in the direction of optical axis XA through the spiral coupling between the male-threaded section 44A of the driving shaft 44 and the female-threaded cylinder 43A of the support member 43.

Figure 6B:
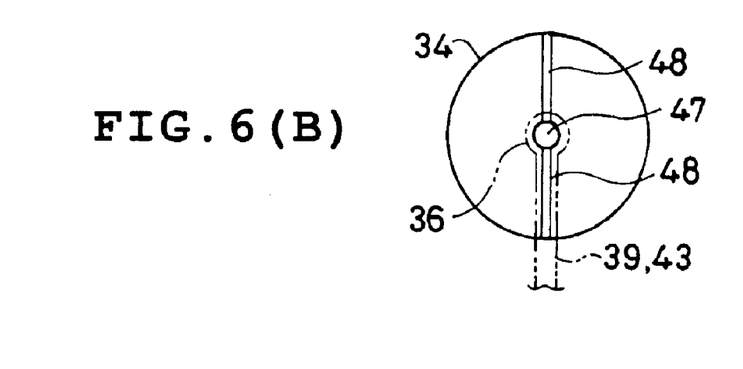
FIG. 6(B) shows an aperture blade placed in front of a light source in the apparatus of FIG. 6(A) when taken from the front.

FIG. 6(B) shows an aperture member placed in front of the light source 34 and in the second embodiment, the aperture blade 36 and the support members 39, 43 themselves are configured to avoid unnecessary shielding. More specifically, as shown in FIG. 6(B), an electrode 47 is supported by a support member 48 in the light source 34 and the electrode 47 and the support member 48 cannot directly transmit any outgoing light. Therefore, the small-circle aperture blade 36 is placed in front of the electrode 47 and the support members 39, 43 of the aperture blade 36 are placed in front of the support member 48, so that the aperture mechanism may not decrease the quantity of light which would be inherently provided by the light source 34.

Figure 9:
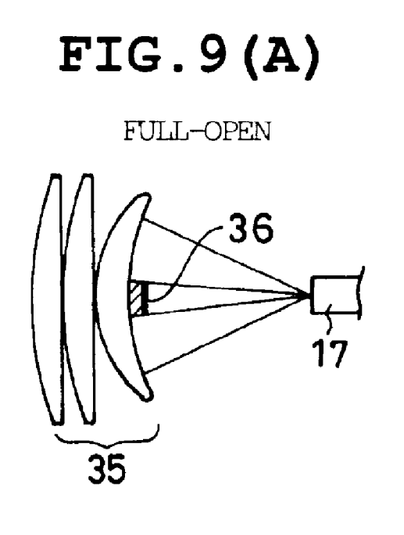
FIGS. 9(A) to 9(D) show how the aperture blade according to the second embodiment shields the ray bundle in each position.

The second embodiment is configured as described above and the above-described aperture blade 36 is driven by the mechanism unit 37 from a full-open position shown in FIG. 9(A) through an intermediate position shown in FIG. 9(B) to a fully-closed position shown in FIG. 9(C). Thus, the ray bundle 100 is shielded as shown by steps 201 to 203 in FIG. (D), thereby achieving shielding (dimming) by the aperture blade 36.

Also for the second embodiment, the outgoing light output from the illumination lens 16 exhibits a wide distribution as shown by the characteristic curve $C_3$ in FIG. 5. When the aperture blade 36 is placed in the full-open position, strictly speaking, it reduces illumination light in the central region (around the optical axis) of the ray bundle 100 to some extent but such reduced illumination light is satisfactory to long-distance examinations as shown by the characteristic curve $C_1$ in FIG. 5, and when the aperture blade 36 shields some of illumination light, the remaining illumination light is satisfactory to short-distance examinations as shown by the characteristic curve $C_3$, thereby providing satisfactorily bright images in whole during not only long-distance but short-distance examinations.

What is claimed is:

1. An endoscope light source apparatus comprising:
    a condensing optical system for condensing source light;
    a light guide for guiding the light from the condensing optical system to the endoscope front end;
    an aperture blade disposed between the light guide and the condensing optical system and which moves in a direction perpendicular to an optical axis of the condensing optical system and which is shaped to have an outline converging toward a front end in a moving direction, to have a base section which is large enough to fully shield a ray bundle from the condensing optical system, to have a front-end blade section which has a width smaller than the diameter of the ray bundle, and to have a front edge which forms a straight line; and
    an aperture driving circuit for driving the aperture blade so that all light in proximity of a central region of the ray bundle is shielded earlier than that in the outer regions during dimming.

2. The endoscope light source apparatus according to claim 1, wherein the aperture blade has an outline converging toward its front end and the shielding width of the front-end blade section is smaller than the diameter of the ray bundle of the source light.

3. The endoscope light source apparatus according to claim 1, wherein when an optical fiber bundle is divided into two at the incident end of the light guide in order to serve two illumination sections on the endoscope front end, the aperture blade rotates along a dividing line between the two optical fiber bundles.

4. An endoscope light source apparatus comprising:
    a condensing optical system for condensing source light;
    a light guide for guiding the light from the condensing optical system to the endoscope front end;
    an aperture blade disposed substantially on the optical axis between the light guide and the condensing optical system and having an area smaller than the cross-sectional area of a ray bundle from the condensing optical system to the light guide; and
    an aperture moving mechanism for moving the aperture blade in the direction of optical axis of the optical system so that all light in proximity of a central region of the ray bundle is shielded earlier than that in the outer regions during dimming.

5. The endoscope light source apparatus according to claim 4, wherein the aperture moving mechanism uses a linear induction motor which moves the aperture blade linearly in the direction of optical axis.

6. The endoscope light source apparatus according to claim 4, wherein the aperture moving mechanism uses a rotary motor and a threaded coupling conversion mechanism for converting a rotational motion of the rotary motor into a linear motion through a threaded coupling structure.

* * * * *